United States Patent [19]

Tokuyama et al.

[11] Patent Number: 4,511,738

[45] Date of Patent: Apr. 16, 1985

[54] PROCESS FOR PREPARING PHOSPHINE OXIDES

[75] Inventors: Kanji Tokuyama; Yasuhiro Nishitani; Mamoru Tanaka, all of Osaka; Wataru Nagata, Hyogo, all of Japan

[73] Assignee: Shionogi & Co., Ltd., Osaka, Japan

[21] Appl. No.: 456,221

[22] Filed: Jan. 7, 1983

[30] Foreign Application Priority Data

Jan. 12, 1982 [JP] Japan .................................. 57/3718

[51] Int. Cl.$^3$ .............................................. C07F 9/54
[52] U.S. Cl. .................................................... 568/14
[58] Field of Search .......................... 568/14; 260/986

[56] References Cited

U.S. PATENT DOCUMENTS 3,082,256  3/1963  Harwood et al. ..................... 568/14
3,267,149  8/1966  Garner .................................. 568/14

*Primary Examiner*—Helen M. S. Sneed
*Attorney, Agent, or Firm*—Birch, Stewart, Kolasch & Birch

[57] ABSTRACT

A phosphine sulfide derivative is chlorinated and hydrolyzed with little pollution problem to give the corresponding phosphine oxide derivative.

15 Claims, No Drawings

PROCESS FOR PREPARING PHOSPHINE OXIDES

This invention relates to a process for preparing a phosphine oxide derivative which comprises chlorinating and hydrolyzing the corresponding phosphine sulfide derivative.

Thousands of tons of triphenylphosphine per year are under use in Japan e.g. aas a desulfurizing reagent. The resulting sulfide is known to be converted into the phosphine oxide derivative which can be easily handled without pollution. For example, treatment of triarylphosphine sulfide with sulfuric acid in refluxing dimethyl sulfoxide gives the objective triarylphosphine oxide, sulfur and dimethyl sulfide (Synthesis, 1973, 307). However, the dimethyl sulfoxide solvent is expensive, the heating requires energy, and the resulting dimethyl sulfide has a terrible odor requiring another excessive anti-pollution treatment. Thus, the reference method can not be used industrially. Triarylphosphine sulfide is also oxidized to give the corresponding oxide with a percarboxylic acid. However, this method is expensive, dangerous and severe. Therefore, it can not be used profitably in large scale.

The present inventors have searched for a method which does not have these disadvantages. They succeeded in finding a new method using an inexpensive reagent at around room temperature under a mild condition and then improved the reaction conditions to comply with various industrial requirements, completing this invention.

In this invention, the phosphine sulfide derivative used as the substrate includes triarylphosphine sulfide, trialkoxyphosphine sulfide and the like, especially trimonocyclic aryl-phosphine sulfide and tri-lower alkoxyphosphine sulfide. More specifically, most preferred are triphenylphosphine sulfide and tri-($C_1$ and $C_5$)-alkyl thionophosphate.

Preferably chlorinating reagents are thionyl chloride, phosphorus pentachloride, chlorine, sodium hypochlorite, potassium hypochlorite, calcium hypochlorite and the like. Other chlorinating reagents can be used. Also, other halogenating reagents can be used, but these are not superior to the chlorinating reagents due to their poor resources and high cost.

The chlorination is carried out usually in a solvent inert to the reagent.

The water used for hydrolysis of the chlorinated intermediate is usually made weakly basic e.g. at pH 7.5 to 9 by adding e.g. an easily available hydroxide, carbonate or bicarbonate of an alkali metal or alkaline earth metal. Usual work up of the chlorinated intermediate may give the hydrolized product. An aqueous hypochlorite salt or other basic chlorinating reagent may also be a reagent for this hydrolysis. The reaction medium can contain an inert solvent.

The chlorinating reagent and the water can be added simultaneously.

The most appropriate reagent is an aqueous hypochlorite solution and, in this case, the objective phosphine oxide can be produced directly without isolating chlorinated intermediates. Thus, the procedure is more convenient and inexpensive.

In a typical procedure, the phosphine sulfide derivative is suspended in 1 to 50 volumes of an ester solvent (e.g. ethyl acetate) or an ether solvent (e.g. dioxane or tetrahydrofuran), mixed with 1 to 10 molar equivalents of a chlorinating reagent (e.g. thionyl chloride, phosphorus oxychloride, phosphorus pentachloride or chlorine) at 0° C. to 40° C. for 10 minutes to 5 hours, and the reaction mixture is washed with an excess amount of aqueous base (e.g. sodium hydroxide, sodium carbonate or sodium hydrogen carbonate) at 0° to 40° C. for 10 minutes to 5 hours to give the objective phosphine oxide.

In another typical procedure, the phosphine sulfide derivative is suspended in a mixture of 1 to 50 volumes of an aqueous base (e.g. sodium hydroxide, sodium carbonate of sodium hydrogen carbonate) and 1 to 50 volumes of $C_1$ to $C_5$-alkanol (e.g. methanol, ethanol, propanol, butanol, isobutanol, n-pentanol or isopentanol) and treated with 1 to 10 molar equivalents of chlorine or aqueous hypochlorite (preferably sodium or calcium hypochlorite) at $-5°$ C. to 100° C. (preferably 0° C. to 40° C.) for 10 minutes to 5 hours (preferably 1 to 2 hours). The amount of the chlorinating reagent is preferably determined by measuring oxidation-reduction potential of the reaction mixture (e.g. by using iodo-starch test strip or polarographic or potentiometric technique) to avoid side reactions due to an excessive amount of the added chlorinating reagent.

The product can be isolated and purified by applying a conventional method e.g. extraction, crystallization, recrystallization or washing.

Following Examples illustrate the embodiment of this invention.

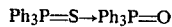
(A)

EXAMPLE 1 (Thionyl chloride)

To a mixture of triphenylphosphine sulfide (0.3 g) and ethyl acetate (10 ml) is added thionyl chloride (0.16 ml) at room temperature, and the mixture is stirred for 2 hours at the same temperature. The reaction mixture is shaken with aqueous 6% sodium hydrogen carbonate (20 ml) and the resulting mass is stirred for another 2 hours. The organic layer which forms on standing for a while is taken, washed with water, filtered to remove a solid mass and concentrated to dryness. The residue is crystallized from ether to give triphenylphosphine oxide (0.26 g). m.p. 155°–156° C.

EXAMPLE 2 (Phosphorus pentachloride)

To a suspension of triphenylphosphine sulfide (0.74 g) in ethyl acetate is added phosphorus pentachloride (1.2 g) under ice cooling, and the mixture is stirred at room temperature for 1 hour. To the mixture is added aqueous 10% sodium carbonate (50 ml) and the resulting mixture is stirred at room temperature for 4 hours. The reaction mixture is worked up in a manner similar to that of Example 1 affording triphenylphosphine oxide (0.70 g). m.p. 154°–156° C.

EXAMPLE 3 (Chlorine gas)

Through a mixture of triphenylphosphine sulfide (11.03 g) and ethyl acetate (200 ml) is bubbled chlorine gas (ca. 2.2 molar equivalents) at room temperature. The resulting mixture is neutralized with aqueous 6% sodium hydrogen carbonate (350 ml) and stirred at room temperature for 10 minutes. The reaction mixture is then worked up as in the case of Example 1 to give triphenylphosphine oxide (10 g). m.p. 154°–157° C.

EXAMPLE 4 (Sodium hypochlorite)

To a mixture of isopropanol (50 ml), triphenylphosphine sulfide (7.0 g) and aqueous 2.5% sodium hydrogen carbonate (15 ml) is added aqueous 6% sodium hypochlorite (90 ml) at 15° to 20° C., and the mixture is stirred for 1.5 hours at 20° C. The organic layer is taken and diluted with water to separate triphenylphosphine oxide as crystals. The precipitate is washed with water and dried to give the product (6.1 g) melting at 154° to 156° C.

EXAMPLE 5 (Calcium hypochlorite)

By substituting the aqueous 6% sodium hypochlorite in Example 4 for a solution of calcium hypochlorite (5.5 g) in water (70 ml), the same product can be obtained.

EXAMPLE 6 (Sodium hypochlorite)

To a mixture of methanol (125 ml), triphenylphosphine sulfide (7.5 g) and aqueous 2.5% sodium hydrogen carbonate (25 ml) is added aqueous 14.3% sodium hypochlorite (125 ml) at 10° C. to 15° C., and the mixture is stirred for 1 hour at the same temperature. The reaction mixture is diluted with water (500 ml), and the separated crystals are collected by filtration, washed with water and dried to give triphenylphosphine oxide (6.5 g). m.p. 154°–157° C.

EXAMPLE 7 (Chlorine gas)

To a mixture of isobutanol (50 ml), triphenylphosphine sulfide (7.0 g) and aqueous 5% sodium hydroxide (50 ml) is bubbled chlorine gas at 15° C. until no appreciable amount of the starting sulfide is detected on thin-layer chromatogram. The reaction mixture is allowed to stand for a while and the organic layer is taken. The layer is washed with water and concentrated to dryness. The residue is triturated with ether to give triphenylphosphine oxide.

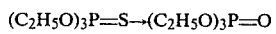

(B)

EXAMPLE 8 (Sodium hypochlorite)

To a mixture of isopropanol (125 ml), triethyl thionophosphate (10.0 g) and aqueous 2% sodium hydrogen carbonate is added aqueous 6% sodium hypochlorite (125 ml), and the mixture is stirred for 30 minutes. The reaction mixture is extracted with ether, and the extract is concentrated to dryness. The residue is distilled under reduced pressure to give triethyl phosphate (8.0 g). bp$_{25}$ 103° C.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What we claim is:

1. A process for preparing a tri-(monocyclic aryl)-phosphine oxide or a tri-lower alkyl phosphate which comprises:
   chlorinating the corresponding tri-(monocyclic aryl)-phosphine sulfide or tri-lower alkyl thionophosphate by treatment with a hypohalite salt or chlorine in an aqueous medium; and
   hydrolyzing by treatment with an aqueous base.

2. A process according to claim 1, wherein the phosphine sulfide is triphenylphosphine sulfide or tri-($C_1$ to $C_5$)-alkyl thionophosphate.

3. A process according to claim 1, wherein the aqueous medium is aqueous methanol, ethanol, propanol, butanol, isobutanol, n-pentanol or isopentanol.

4. A process according to claim 1, wherein said chlorination is effected at a temperature of from 0° to 40° C. in 1 to 50 volumes of said aqueous medium with 1 to 10 molar equivalents of said hypohalite salt or chlorine; and said hydrolysis is effected at a temperature of from 0° to 40° C. by treatment with a hydroxide, carbonate or bicarbonate of an alkali metal or alkaline earth metal.

5. A process according to claim 4, wherein said hydrolysis is effected at a pH of 7.5 to 9.

6. A process according to claim 1, wherein said chlorination and hydrolysis are effected simultaneously.

7. A process according to claim 1 wherein the chlorinating reagent is a hypochlorite salt.

8. A process according to claim 1 wherein the chlorination is effected with 1 to 10 molar equivalents of the chlorinating reagent.

9. A process according to claim 1 wherein the chlorination time is 10 minutes to 5 hours.

10. A process according to claim 1 wherein the chlorination is effected at a temperature range between 0° C. to 40° C.

11. A process according to claim 1 wherein the chlorination is carried out in 1 to 50 volumes of the solvent.

12. A process according to claim 1 wherein the hydrolyzing reagent is an aqueous solution of a hydroxide, carbonate or bicarbonate of an alkali metal or alkaline earth metal.

13. A process according to claim 12 wherein the alkali metal is sodium.

14. A process according to claim 1 wherein the hydrolysis time is 10 minutes to 5 hours.

15. A process according to claim 1 wherein the hydrolysis is effected at a temperature range between 0° C. to 40° C.

* * * * *